United States Patent
Liu et al.

(10) Patent No.: US 9,365,481 B2
(45) Date of Patent: Jun. 14, 2016

(54) CYCLOHEXENONE COMPOSITIONS AND PROCESS FOR MAKING THEREOF

(71) Applicant: Golden Biotechnology Corporation, Jersey City, NJ (US)

(72) Inventors: Sheng-Yung Liu, New Taipei (TW); Wu-Che Wen, New Taipei (TW); Chih-Ming Chen, New Taipei (TW); Hsiu-Yi Cheng, New Taipei (TW)

(73) Assignee: Golden Biotechnology Corporation, Jersey City, NJ (US)

( * ) Notice: Subject to any disclaimer, the term of this patent is extended or adjusted under 35 U.S.C. 154(b) by 0 days.

(21) Appl. No.: 14/184,954

(22) Filed: Feb. 20, 2014

(65) Prior Publication Data
US 2015/0018567 A1    Jan. 15, 2015

Related U.S. Application Data

(60) Provisional application No. 61/767,212, filed on Feb. 20, 2013.

(51) Int. Cl.
*C07C 49/753*    (2006.01)
*C07D 307/20*    (2006.01)
*C07C 45/00*    (2006.01)
*C07C 45/61*    (2006.01)

(52) U.S. Cl.
CPC ............... *C07C 49/753* (2013.01); *C07C 45/00* (2013.01); *C07C 45/61* (2013.01); *C07D 307/20* (2013.01)

(58) Field of Classification Search
None
See application file for complete search history.

(56) References Cited

U.S. PATENT DOCUMENTS

2011/0059123 A1 * 3/2011 Liu et al. .................. 424/195.15
2011/0060058 A1 * 3/2011 Liu et al. ....................... 514/690

OTHER PUBLICATIONS

Database CAPLUS in STN, Acc. No. 1987:598673, D'Ambrosio et al., Helvetica Chimica Acta (1986), 69(7), pp. 1581-1584 (abstract).*

* cited by examiner

*Primary Examiner* — Brian J Davis
(74) *Attorney, Agent, or Firm* — Chang-Hsing Liang

(57) ABSTRACT

Provided herein are processes of preparing cyclohexenone compounds useful for cancer treatments and/or diseases.

13 Claims, No Drawings

CYCLOHEXENONE COMPOSITIONS AND PROCESS FOR MAKING THEREOF

BACKGROUND OF THE INVENTION

The present disclosure relates to composition and processes of preparing cyclohexenone compounds.

SUMMARY OF THE INVENTION

In one aspect, there are provided a process for preparing a compound of formula I:

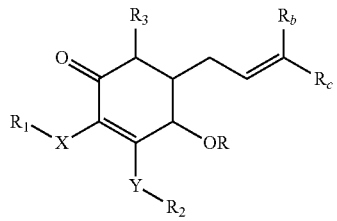

(I)

comprising a step of reacting a compound of formula II,

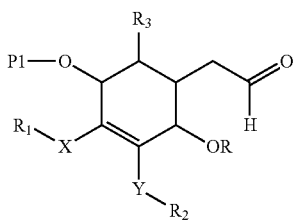

(II)

with a compound of formula (III), $Ph_3PCHR_bR_cL$ (III) in the presence of a base, wherein L is a leaving group, P1 is a hydroxyl protecting group;

each of X and Y independently is a bond, oxygen, $NR_5$ or sulfur;

R is H, $C(=O)OR_5$, $C(=O)R_5$, $C(=O)NR_5R_6$, $C(=O)SR_5$, $C(=S)R_5$, or $C(=S)NR_5R_6$;

each of $R_1$, $R_2$ and $R_3$ independently is H, or an optionally substituted $C_1$-$C_{12}$alkyl;

each of $R_b$ and $R_c$ independently is an optionally substituted $C_1$-$C_{12}$alkyl or $(CH_2CH=C(CH_3)(CH_2))_m$—$R_4$, wherein $R_4$ is H, $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently H or $C_1$-$C_8$alkyl;

$R_7$ is a $C_1$-$C_8$alkyl, $OR_5$ or $NR_5R_6$;

m=0-11.

In another aspect, there are provided processes for preparing a compound of formula Ia:

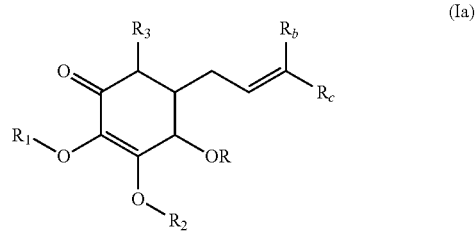

(Ia)

comprising a step of reacting a compound of formula IIa,

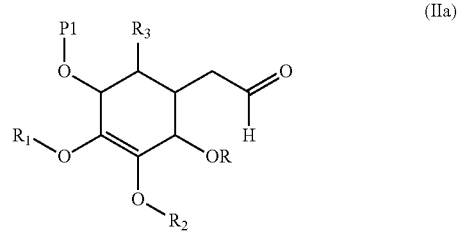

(IIa)

with a compound of formula (III), $Ph_3PCHR_bR_cL$ (III) in the presence of a base, wherein L is a leaving group, P1 is a hydroxyl protecting group;

R is H, $C(=O)OR_5$, $C(=O)R_5$, $C(=O)NR_5R_6$, $C(=O)SR_5$, $C(=S)R_5$, or $C(=S)NR_5R_6$;

each of $R_1$, $R_2$ and $R_3$ independently is H, or an optionally substituted $C_1$-$C_{12}$alkyl;

each of $R_b$ and $R_c$ independently is an optionally substituted $C_1$-$C_{12}$alkyl or $(CH_2CH=C(CH_3)(CH_2))_m$—$R_4$, wherein $R_4$ is H, $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently H or $C_1$-$C_8$alkyl;

$R_7$ is a $C_1$-$C_8$alkyl, $OR_5$ or $NR_5R_6$;

m=0-11.

In another aspect of the present invention, there are provided processes for preparing a compound of formula IV:

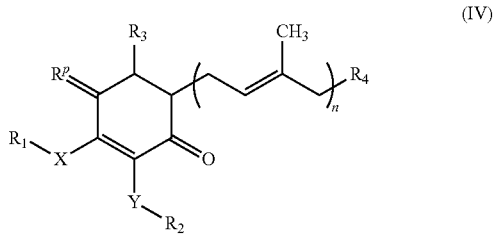

(IV)

comprising reacting an enol or enolate compound of formula V,

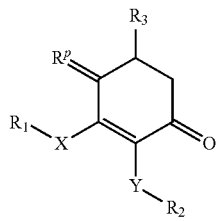

with a compound of formula (VI),

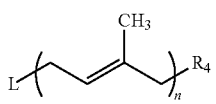

under suitable conditions, wherein each of X and Y independently is a bond, oxygen, $NR_5$ or sulfur;

$R^p$ is an oxo protecting group;

L is a leaving group;

each of $R_1$, $R_2$ and $R_3$ independently is H, or an optionally substituted $C_1$-$C_{12}$alkyl;

$R_4$ is H, $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently H or $C_1$-$C_8$alkyl;

$R_7$ is a $C_1$-$C_8$alkyl, $OR_5$ or $NR_5R_6$;

and n=1-12.

In another aspect of the present invention, there are provided processes for preparing a compound of formula IVa:

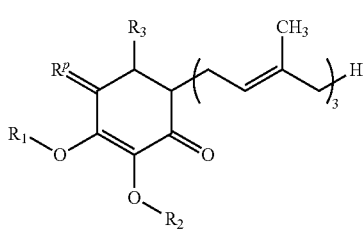

comprising reacting an enol or enolate compound of formula V,

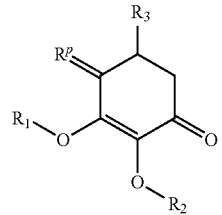

with a compound of formula (VIa),

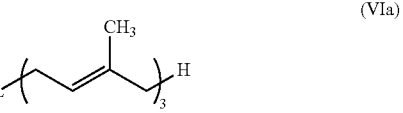

under suitable conditions, wherein $R^P$ is an oxo protecting group;

L is a leaving group; and each of $R_1$, $R_2$ and $R_3$ independently is H, or an optionally substituted $C_1$-$C_{12}$alkyl.

In one aspect, there are provided a compound of formula X:

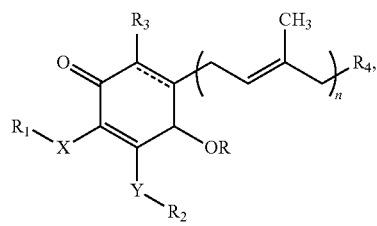

or a pharmaceutically acceptable salt, metabolite, solvate or prodrug thereof, wherein each of X and Y independently is a bond, oxygen, $NR_5$ or sulfur;

R is H, $C(=O)OR_5$, $C(=O)R_5$, $C(=O)NR_5R_6$, $C(=O)SR_5$, $C(=S)R_5$, or $C(=S)NR_5R_6$;

each of $R_1$, $R_2$ and $R_3$ independently is H, or an optionally substituted $C_1$-$C_{12}$alkyl;

$R_4$ is H, $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_1$ and $R_6$ is independently H or $C_1$-$C_8$alkyl;

$R_7$ is a $C_1$-$C_8$alkyl, $OR_5$ or $NR_5R_6$; the dotted line denotes an optionally present bond;

and n=1-12, provided when X and Y are oxygen, each of $R_1$ and $R_2$ independently is a substituted $C_1$-$C_{12}$alkyl.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Cyclohexenone compounds may be isolated from the extracts of *Antrodia camphorata*. For example, Compounds 1, and 3-7 are isolated from organic solvent extracts.

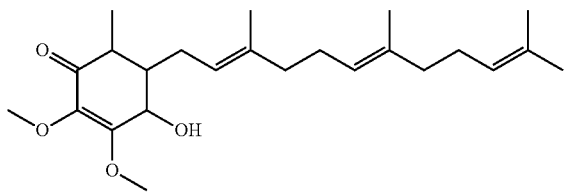

1

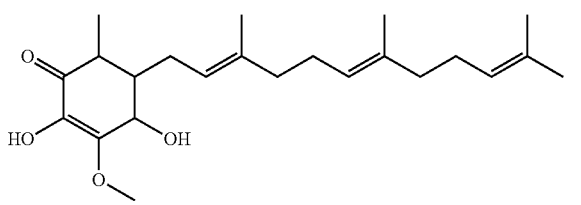

3

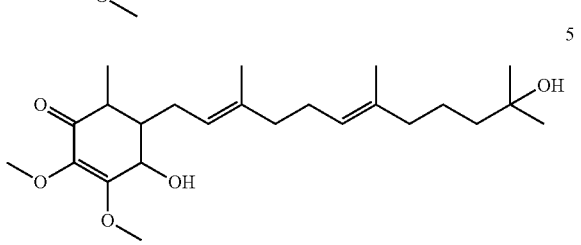

5

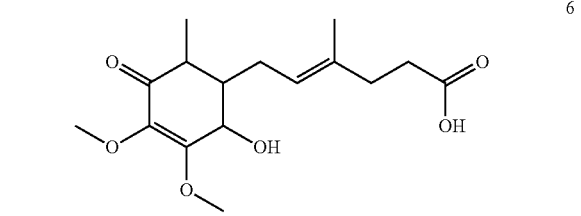

7

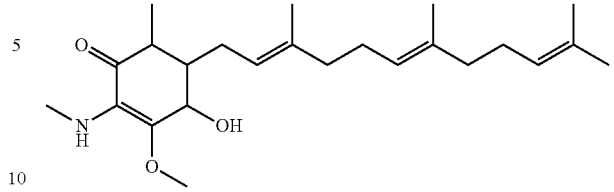

8

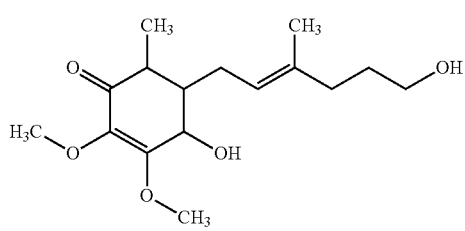

2

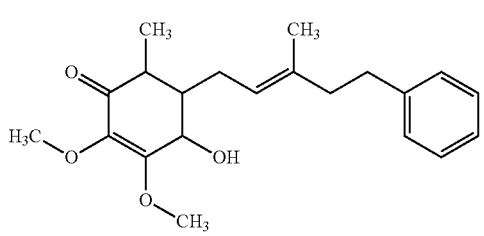

9

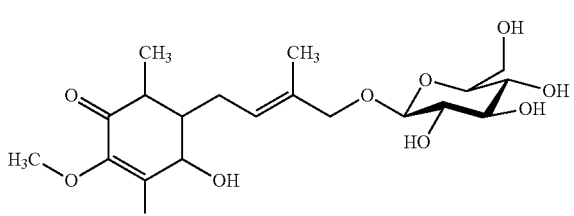

10

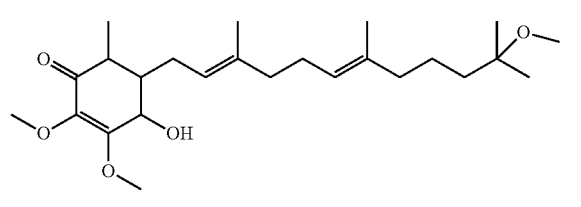

11

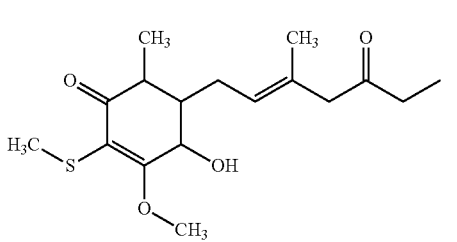

12

In some embodiments, certain cyclohexenone compounds can be prepared synthetically. The following are some non-limited examples.

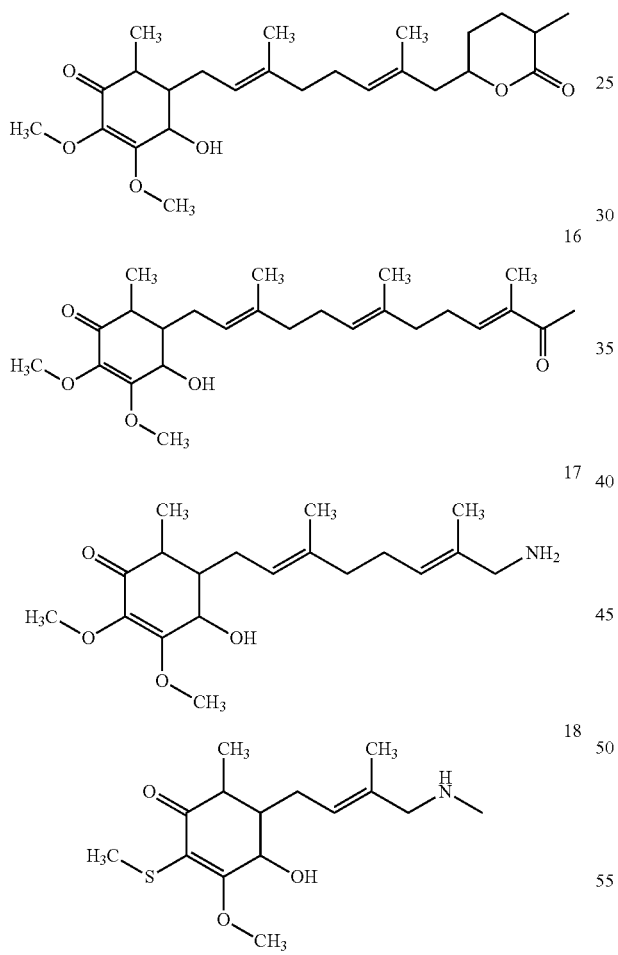
Many cyclohexenone compounds isolated from the extracts of *Antrodia camphorata* provide certain biological effects. In particular, Compounds 25 to 31 were prepared and tested against Compound 1 to determine their biological properties.

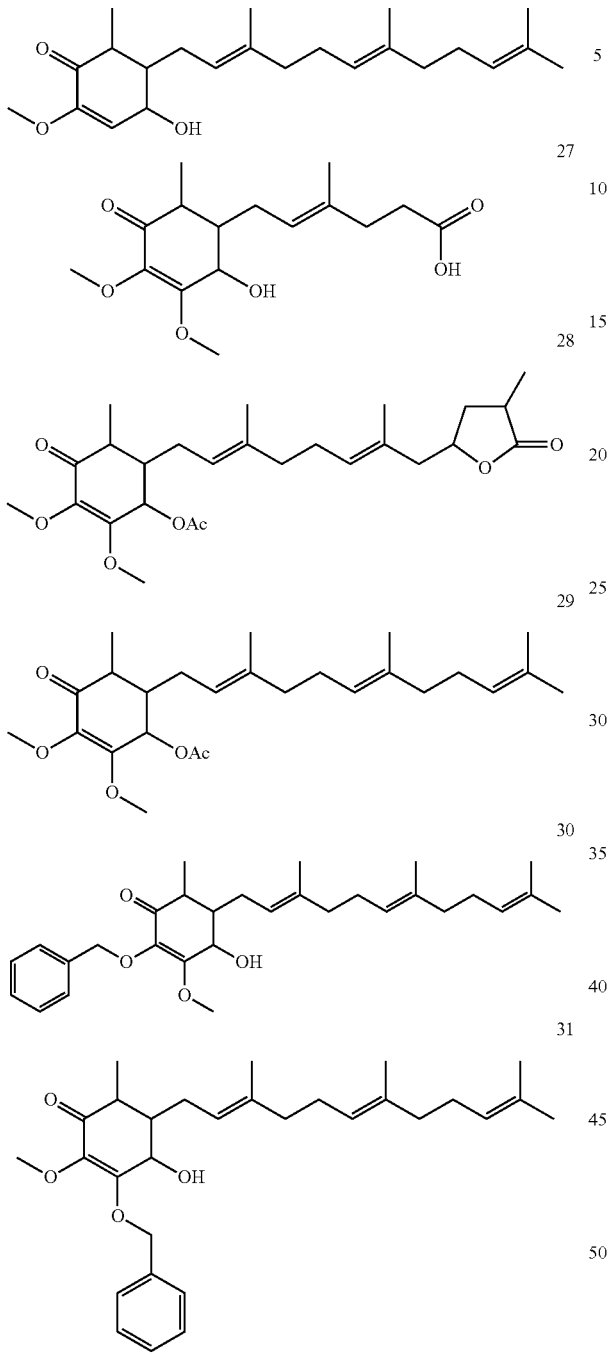

In some embodiments, there are provided a compound of formula X:

(X)

or a pharmaceutically acceptable salt, metabolite, solvate or prodrug thereof, wherein the dotted line of the ring is either a single or double bond;

each of X and Y independently is a bond, oxygen, $NR_5$ or sulfur;

R is H, $C(=O)OR_5$, $C(=O)R_5$, $C(=O)NR_5R_6$, $C(=O)SR_5$, $C(=S)R_5$, or $C(=S)NR_5R_6$;

each of $R_1$, $R_2$ and $R_3$ independently is H, or an optionally substituted $C_1$-$C_{12}$alkyl;

$R_4$ is H, $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently H or $C_1$-$C_8$alkyl;

$R_7$ is a $C_1$-$C_8$alkyl, $OR_5$ or $NR_5R_6$; the dotted line denotes an optionally present bond;

and n=1-12, provided when X and Y are oxygen, each of $R_1$ and $R_2$ independently is a substituted $C_1$-$C_{12}$alkyl.

In certain embodiments, the compound of formula (X) is isolated from the organic solvent extracts of *Antrodia camphorata*. In some embodiments, the organic solvent is selected from alcohols (e.g., methanol, ethanol, propanol, or the like), esters (e.g., methyl acetate, ethyl acetate, or the like), alkanes (e.g., pentane, hexane, heptane, or the like), halogenated alkanes (e.g., chloromethane, chloroethane, chloroform, methylene chloride, and the like), and the like. In certain embodiments, the organic solvent is alcohol. In certain embodiments, the alcohol is ethanol. In some embodiments, the compound of formula (X) is isolated from the aqueous extracts of *Antrodia camphorata*. In some embodiments, the compound of formula (X) is prepared synthetically by the disclosed method herein. In other embodiments, the compound of formula (X) is prepared by other methods readily available in the art such as via synthetic or semi-synthetic methods.

In some embodiments, each of X and Y independently is a bond. In some embodiments, R is H, $C(=O)OR_5$, $C(=O)R_5$, $C(=O)NR_5R_6$. In certain embodiments, R is H, or $C(=O)R_5$. In certain embodiments, R is H, $C(=O)C_3H_7$, $C(=O)C_2H_5$, or $C(=O)CH_3$. In some embodiments, each of $R_1$, $R_2$ and $R_3$ independently is hydrogen, or a substituted $C_1$-$C_{12}$alkyl. In some embodiments, each of $R_1$, $R_2$ and $R_3$ independently is hydrogen, or an aryl or heteroaryl substituted $C_1$-$C_{12}$alkyl. In certain embodiments, $R_1$ is methyl, ethyl, propyl, butyl, pentyl or hexyl substituted with phenyl or pyridinyl. In certain embodiments, $R_1$ is a $CH_2$-Ph. In certain embodiments, $R_1$ is H, methyl, ethyl, propyl, butyl, pentyl or hexyl provided one of X and Y is a bond. In certain embodiments, $R_2$ is methyl, ethyl, propyl, butyl, pentyl or hexyl substituted with phenyl or pyridinyl. In certain embodiments, $R_2$ is $CH_2$-Ph. In certain embodiments, $R_2$ is H, methyl, ethyl, propyl, butyl, pentyl or hexyl provided one of X and Y is a bond. In some embodiments, $R_3$ is H, methyl, ethyl, propyl, butyl, pentyl or hexyl. In some embodiments, $R_4$ is H, halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$. In some embodiments, $R_4$ is $C_2H_4C(CH_3)_2OH$, $C_2H_4C(CH_3)_2OCH_3$, $CH_2COOH$, $C_2H_4COOH$, $CH_2OH$, $C_2H_4OH$, $CH_2Ph$, $C_2H_4Ph$, $CH_2CH=C(CH_3)(CHO)$, $CH_2CH=C(CH_3)(C(=O)CH_3)$, 5 or 6-membered lactone, $C_2$-$C_8$ alkenyl, $C_2$-$C_8$ alkynyl, aryl, and glucosyl, wherein the 5 or 6-membered lactone, $C_2$-$C_8$ alkenyl, $C_2$-$C_8$ alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl. In certain embodiments, $R_4$ is $CH_2CH=C(CH_3)_2$. In certain embodiments, the compound of formula (X) is selected from group consisting of

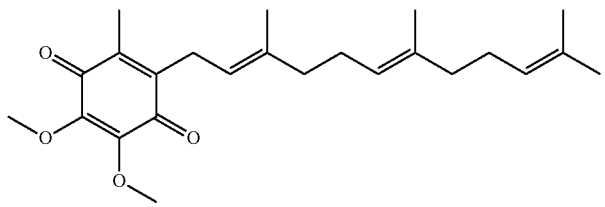

,

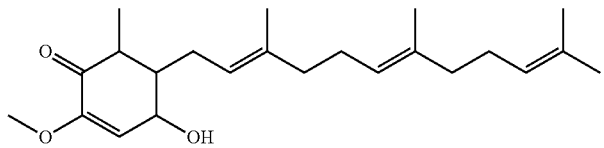

,

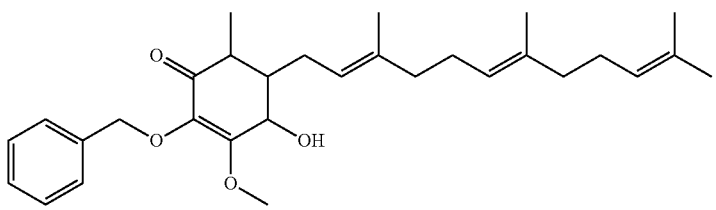

, and

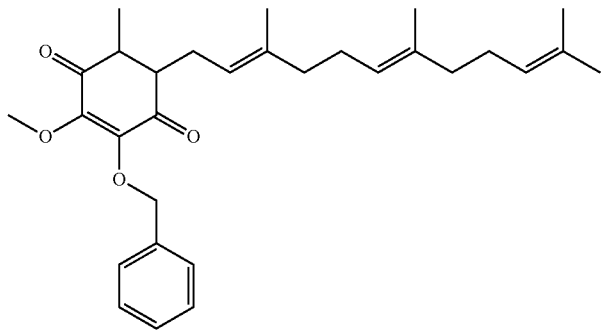

.

Due to the high cost of obtaining cyclohexnone compounds from *Antrodia camphorata* by purification, and/or to prepare desired analogs for further clinical testing, synthetic processes of preparing cyclohexnone compounds are described herein.

In accordance with the present invention, there are provided processes for preparing a compound of formula I:

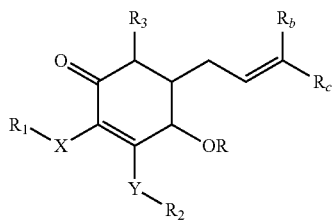
(I)

comprising a step of reacting a compound of formula (II),

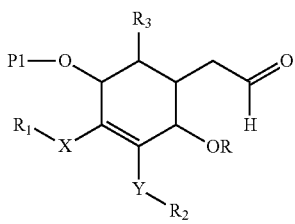
(II)

with a compound of formula (III), $Ph_3PCHR_bR_cL$ (III) in the presence of a base, wherein L is a leaving group, P1 is a hydroxyl protecting group;

each of X and Y independently is a bond, oxygen, $NR_5$ or sulfur;

R is H, C(=O)$OR_5$, C(=O)$R_5$, C(=O)$NR_5R_6$, C(=O)$SR_5$, C(=S)$R_5$, or C(=S)$NR_5R_6$;

each of $R_1$, $R_2$ and $R_3$ independently is H, or an optionally substituted $C_1$-$C_{12}$alkyl;

each of $R_b$ and $R_c$ independently is hydrogen, $C_1$-$C_{12}$alkyl, optionally substituted with ($CH_2CH=C(CH_3)$ $(CH_2))_m$—$R_4$, wherein $R_4$ is hydrogen, $NR_5R_6$, $OR_5$, OC(=O)$R_7$, C(=O)$OR_5$, C(=O)$R_5$, C(=O)$NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, OC(O)$R_7$, C(=O)$OR_5$, C(=O)$R_5$, C(=O)$NR_5R_6$, $C_1$-$C_8$ alkyl, $C_2$-$C_8$ alkenyl, $C_2$-$C_8$ alkynyl, $C_3$-$C_8$cycloalkyl, and $C_1$-$C_8$ haloalkyl;

each of $R_5$ and $R_6$ is independently H or $C_1$-$C_8$alkyl;

$R_7$ is a $C_1$-$C_8$alkyl, $OR_5$ or $NR_5R_6$;

m=0-11. In certain embodiments, R is a hydroxyl protecting group such as a silyl protecting group, and other suitable protecting groups same of different from P1.

The reaction between a compound of formula (II) and a compound of formula (III) is known as Wittig reaction. Since aldehydes, in general, are not chemically stable, the compounds of formula (II) in some embodiments, are prepared in situ. Scheme I provides a non-limited exemplary route to prepare a compound of formula (I). Protection of the free hydroxyl group of Compound 35 follows by reduction of the lactone ring to afford the aldehyde compound of formula (II), which then undergo Wittig reaction with $Ph_3PCHR_bR_cI$ to prepare intermediate A. After deprotection and oxidation, Compound B (which is a compound of formula (I)) is prepared. Compound 36 where R is H can be easily prepared by deprotection reaction.

Scheme I. Exemplary synthetic scheme to prepare a compound of formula (I)

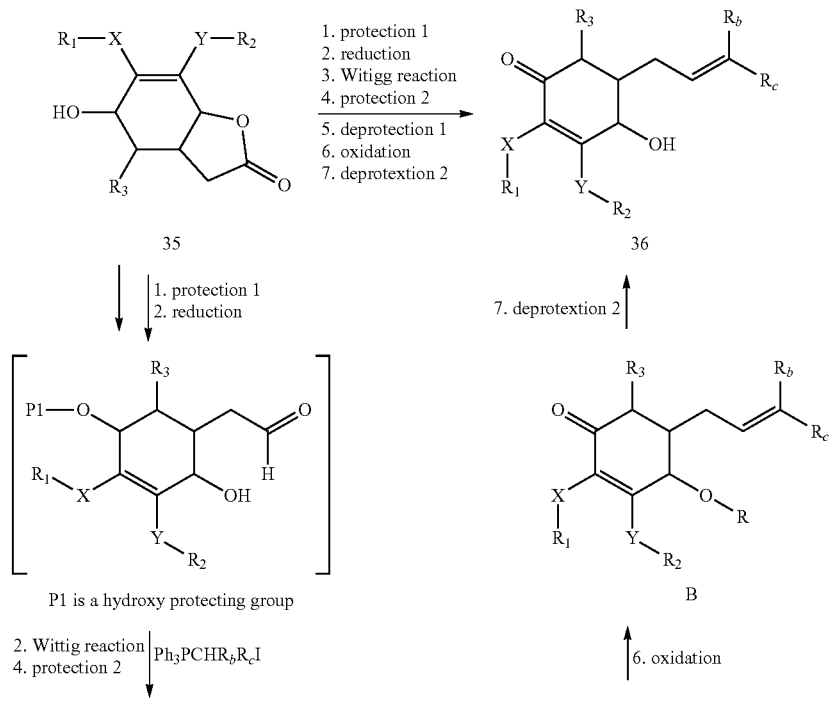

-continued

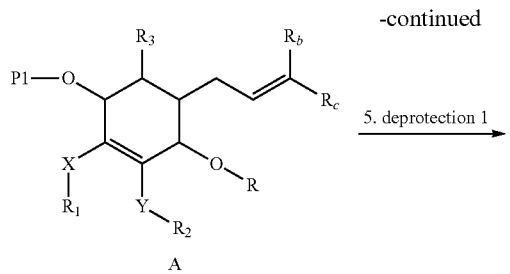 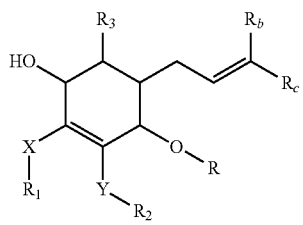

5. deprotection 1

A

An aldehyde can be prepared from reduction of acylsilanes, carboxylic acids, acid halides, anhydride, esters, lactones, amides, nitriles, or the like. In some instances, an aldehyde can be prepared from oxidation of a free hydroxyl group. A skilled person in the art can readily consider other suitable reaction based on this invention to prepare a compound of formula (II). In some embodiments, a compound of formula (II),

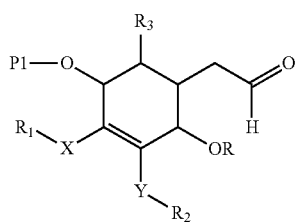
(II)

is prepared from reduction of a compound having the structure of

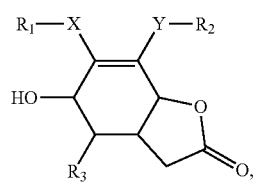

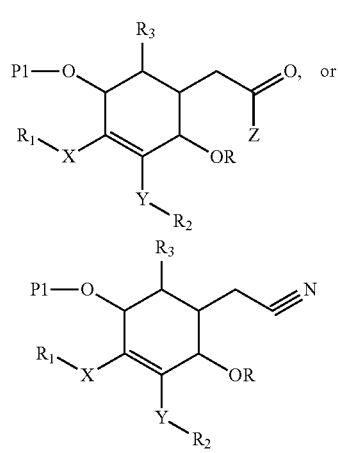

wherein Z is halogen, $OR_5OC(=O)R_7$, or $NR_5R_6$.

In some embodiments, a compound of formula (II),

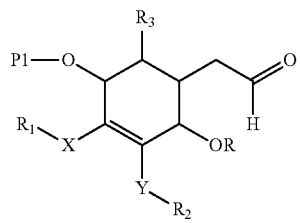
(II)

is prepared from oxidation of a compound having the structure of

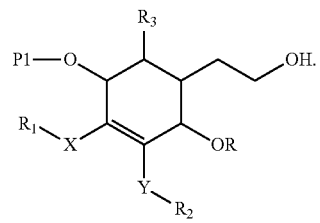

In some embodiments, R is any suitable hydroxyl protecting group that can survive Wittig reaction conditions. For example, R is $C(=O)OR_5$, $C(=O)R_5$, $C(=O)NR_5R_6$, $C(=O)SR_5$, $C(=S)R_5$, $C(=S)NR_5R_6$, or the like.

In some embodiments, said base is a base that can form an ylide from a compound of formula (III), for example, n-butyllithium (n-BuLi), or the like.

In some embodiments, each of $R_1$, $R_2$ and $R_3$ independently is H, methyl, ethyl, propyl, butyl, pentyl or hexyl optionally substituted with an aryl or heteroaryl. In certain embodiments, each of $R_1$, $R_2$ and $R_3$ independently is H, or methyl.

The Wittig reaction provided herein is applicable to many isoprene unit precursors. For example, the reaction is applicable where $R_b$ is $CH_3$ and $R_c$ is $CH_2$ substituted with $(CH_2CH=C(CH_3)(CH_2))_m—R_4$, wherein is $R_4$ is hydrogen $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl; each of $R_5$ and $R_6$ is independently H or $C_1$-$C_8$alkyl; and $R_7$ is a $C_1$-$C_8$alkyl, $OR_5$ or $NR_5R_6$.

For example, without limitation, a skilled artisan may use the following isoprene precursors where P1 is a hydroxy protecting group.

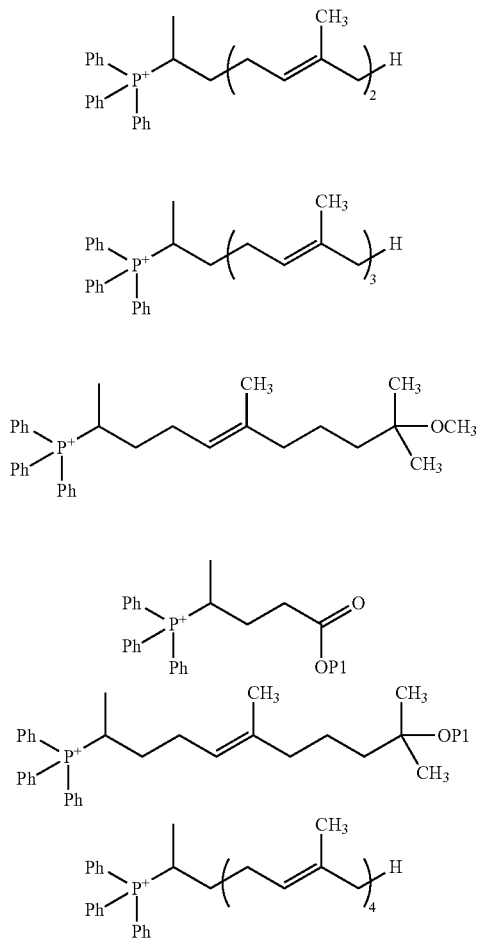

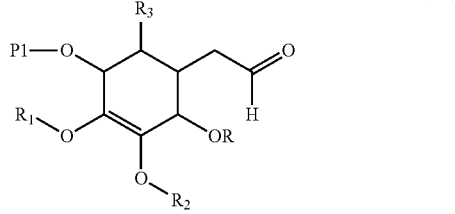

In some embodiments, there are provided processes of preparing compounds of formula (I) wherein X is oxygen, $NR_5$ or sulfur. For example, X may be O, S, NH, $NCH_3$, $NC_2H_5$, or the like.

In other embodiments, there are provided processes of preparing compounds of formula (I) wherein Y is oxygen, $NR_5$ or sulfur. For example, Y may be O, S, NH, $NCH_3$, $NC_2H_5$, or the like.

In other embodiments, there are provided processes of preparing compounds of formula (I) wherein X is O and Y is O, or X is O and Y is S, or X is S and Y is O, or X is O and Y is NH, or X is NH and Y is O.

In some embodiments, there are provided processes for preparing a compound of formula (Ia):

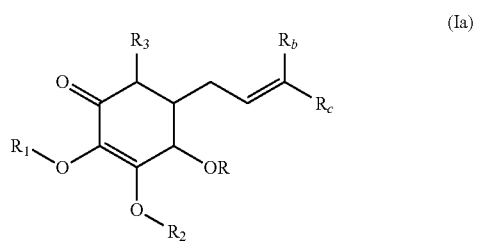

comprising a step of reacting a compound of formula IIa,

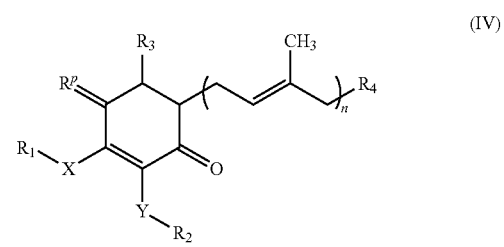

with a compound of formula (III), $Ph_3PCHR_bR_cL$ (II) in the presence of a base, wherein wherein L is a leaving group, P1 is a hydroxyl protecting group;

R is H, $C(=O)OR_5$, $C(=O)R_5$, $C(=O)NR_5R_6$, $C(=O)SR_5$, $C(=S)R_5$, or $C(=S)NR_5R_6$;

each of $R_1$, $R_2$ and $R_3$ independently is H, or an optionally substituted $C_1$-$C_{12}$alkyl;

each of $R_b$ and $R_c$ independently is hydrogen, $C_1$-$C_{12}$alkyl, optionally substituted with $(CH_2CH=C(CH_3)(CH_2))_m$—$R_4$, wherein $R_4$ is $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein 5 or 6-membered lactone, $C_1$-$C_8$alkyl, $C_2$-$C_8$alkenyl, $C_2$-$C_8$alkynyl, aryl, and glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently H or $C_1$-$C_8$alkyl;

$R_7$ is a $C_1$-$C_8$alkyl, $OR_5$ or $NR_5R_6$;

m=0-11.

In some embodiments, there are provided processes of preparing compounds of formula (I) or (Ia) wherein R is H or —$C(=O)C_1$-$C_8$alkyl and each of $R_1$, $R_2$ and $R_3$ independently is H, or $C_1$-$C_{12}$alkyl.

In certain embodiments, R is H, methyl, ethyl, propyl, butyl, pentyl, or the like. In certain embodiments, $R_1$, is H, methyl, ethyl, propyl, butyl, pentyl, or the like. In certain embodiments, $R_2$ is H, methyl, ethyl, propyl, butyl, pentyl, or the like. In certain embodiments, $R_3$ is H, methyl, ethyl, propyl, butyl, pentyl, or the like.

In some embodiments, there are provided processes for preparing a compound of formula IV:

comprising reacting an enol or enolate compound of formula V.

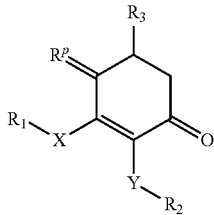

with a compound of formula (VI),

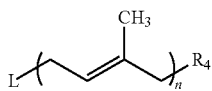

under suitable conditions, wherein
each of X and Y independently is a bond, oxygen, NR$_5$ or sulfur;
R$^P$ is an oxo protecting group;
L is a leaving group;
each of R$_1$, R$_2$ and R$_3$ independently is H, or an optionally substituted C$_1$-C$_{12}$alkyl;
R$_4$ is H, NR$_5$R$_6$, OR$_5$, OC(=O)R$_7$, C(=O)OR$_5$, C(=O)R$_5$, C(=O)NR$_5$R$_6$, halogen, 5 or 6-membered lactone, C$_1$-C$_8$alkyl, C$_2$-C$_8$alkenyl, C$_2$-C$_8$alkynyl, aryl, glucosyl, wherein the 5 or 6-membered lactone, C$_1$-C$_8$alkyl, C$_2$-C$_8$alkenyl, C$_2$-C$_8$alkynyl, aryl, and glucosyl are optionally substituted with one or more substituents selected from NR$_5$R$_6$, OR$_5$, OC(=O)R$_7$, C(=O)OR$_5$C(=O)R$_5$, C(=O)NR$_5$R$_6$, C$_1$-C$_8$ alkyl, C$_2$-C$_8$ alkenyl, C$_2$-C$_8$ alkynyl, C$_3$-C$_8$cycloalkyl, and C$_1$-C$_8$ haloalkyl;
each of R$_5$ and R$_6$ is independently H or C$_1$-C$_8$alkyl;
R$_7$ is a C$_1$-C$_8$alkyl, OR$_5$ or NR$_5$R$_6$;
and n=1-12.
In some embodiments, the enol compound of formula V,

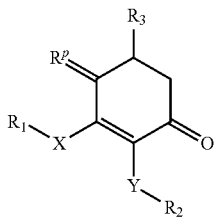

is prepared under suitable conditions (e.g., acid promotion or silyl trapping).

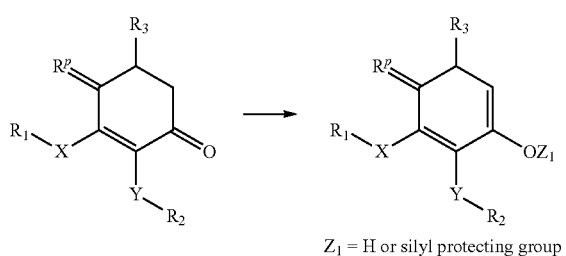

Z$_1$ = H or silyl protecting group

In some embodiments, the enolate compound of formula V,

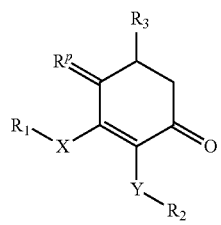

is prepared by reacting a compound of formula V with a strong base. A skilled artisan will readily find other suitable conditions follows the known procedure to prepare the enol or enolate compound of formula V.

In certain embodiments, P is an oxo protecting group that can withstand the acidic or basic conditions for generating enol or enolate compound of Formula V. For example, P is an acyclic or cyclic ketal or an acylic or cyclic thioketal that is stable to aqueous and nonaqueous bases, to nucleophiles including organometallic reagents and to hydride reduction. In some embodiments, P is an acyclic or cyclic thioketal that is stable to aqueous and nonaqueous acids, to nucleophiles including organometallic reagents and to hydride reduction. In certain embodiments, P is 1,3-dithiolane, or the like.

In some embodiments, L is a leaving group that undergoes either SN1, SN2 or SNi reaction under suitable conditions. For example, L is a halogen such as Cl, Br or I. In some instances, L is hydroxyl derived leaving group such as a tosylate or methlate. Other suitable leaving groups may be used by a skilled artisan follows the readily available known procedure.

In some embodiments, there are provided processes of preparing compounds of formula (IV), wherein X is oxygen, NR$_5$ or sulfur. For example, X may be O, S, NH, NCH$_3$, NC$_2$H$_5$, or the like.

In other embodiments, there are provided processes of preparing compounds of formula (IV) wherein Y is oxygen, NR$_5$ or sulfur. For example, Y may be O, S, NH, NCH$_3$, NC$_2$H$_5$, or the like.

In other embodiments, there are provided processes of preparing compounds of formula (IV) wherein X is O and Y is O, or X is O and Y is S, or X is S and Y is O, or X is O and Y is NH, or X is NH and Y is O.

In some embodiments, there are provided processes for preparing a compound of formula IVa:

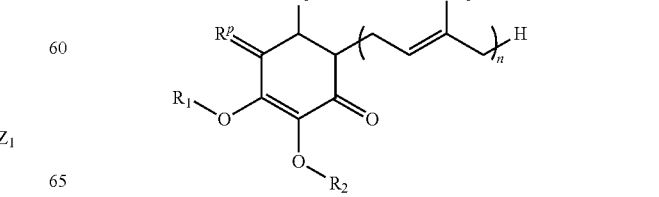

comprising reacting an enol or enolate compound of formula V,

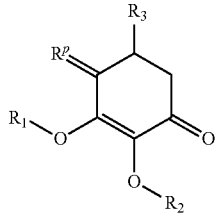
(Va)

with a compound of formula (VIa),

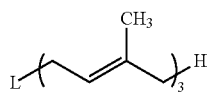
(VIa)

under suitable conditions, wherein
$R^P$ is an oxo protecting group;
L is a leaving group; and
each of $R_1$, $R_2$ and $R_3$ independently is H, or an optionally substituted $C_1$-$C_{12}$alkyl.

In some embodiments, there are provided processes of preparing compounds of formula (IV) or (IVa) wherein R is H or —C(═O)$C_1$-$C_8$alkyl and each of $R_1$, $R_2$ and $R_3$ independently is H, or $C_1$-$C_{12}$alkyl.

In certain embodiments, R is H, methyl, ethyl, propyl, butyl, pentyl, or the like. In certain embodiments, $R_1$ is H, methyl, ethyl, propyl, butyl, pentyl, or the like. In certain embodiments, $R_2$ is H, methyl, ethyl, propyl, butyl, pentyl, or the like. In certain embodiments, $R_3$ is H, methyl, ethyl, propyl, butyl, pentyl, or the like.

Formation of Covalent Linkages by Reaction of an Electrophile with a Nucleophile In certain embodiments, the compounds described herein are modified using various electrophiles or nucleophiles to form new functional groups or substituents. Table 1 entitled "Examples of Covalent Linkages and Precursors Thereof" lists selected, non-limiting examples of covalent linkages and precursor functional groups that are used to prepare the modified compounds. Precursor functional groups are shown as electrophilic groups and nucleophilic groups.

TABLE 1

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

Use of Protecting Groups

In the reactions described, it is necessary in certain embodiments to protect reactive functional groups, for example hydroxy, amino, thiol or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group is removable by a different means. Protective groups that are cleaved under totally disparate reaction conditions fulfill the requirement of differential removal. In some embodiments, protective groups are removed by acid, base, and/or hydrogenolysis. Groups such as trityl, dimethoxytrityl, acetal and t-butyldimethylsilyl are acid labile and are used in certain embodiments to protect carboxy and hydroxy reactive moieties in the presence of amino groups protected with Cbz groups, which are removable by hydrogenolysis, and/or Fmoc groups, which are base labile. In other embodiments, carboxylic acid and hydroxy reactive moieties are blocked with base labile groups such as, but not limited to, methyl, ethyl, and acetyl in the presence of amines blocked with acid labile groups such as t-butyl carbamate or with carbamates that are both acid and base stable but hydrolytically removable.

In another embodiment, carboxylic acid and hydroxy reactive moieties are blocked with hydrolytically removable protective groups such as the benzyl group, while amine groups capable of hydrogen bonding with acids are blocked with base labile groups such as Fmoc. In another embodiment, carboxylic acid reactive moieties are protected by conversion to simple ester compounds as exemplified herein, or they are, in yet another embodiment, blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are optionally subsequently removed by metal or pi-acid catalysts. For example, an allyl-blocked carboxylic acid is optionally deprotected with a Pd(0)-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and cannot react. Once released from the resin, the functional group is available to react.

Typically blocking/protecting groups are, by way of example only:

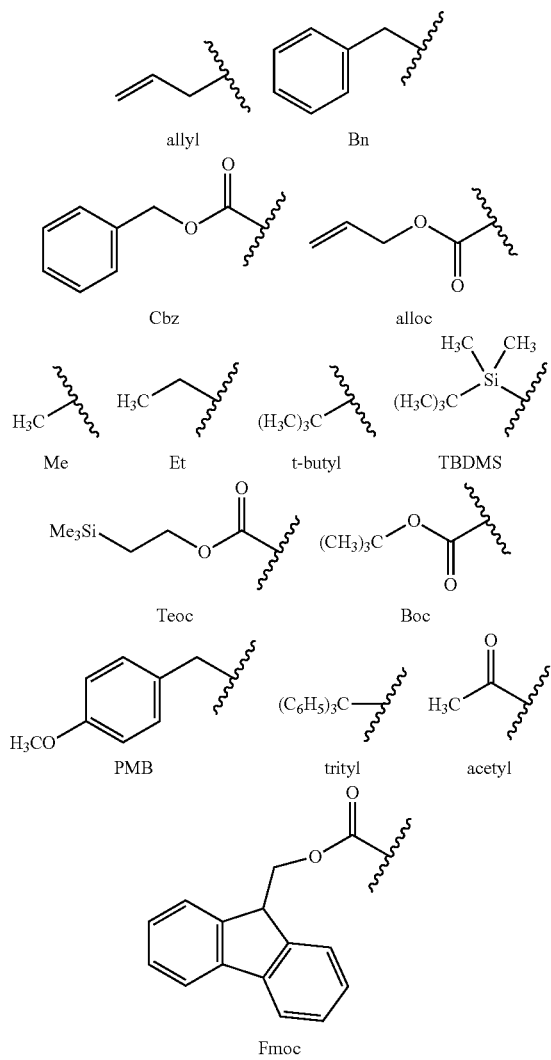

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound provided herein with acids. Pharmaceutically acceptable salts are also obtained by reacting a compound provided herein with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

The term "leaving group" as used herein may be any group which is usually known as a leaving group in organic synthesis, without limitation, for example: halogens such as fluorine, chlorine, bromine and iodine, alkylsulfonyloxy groups such as methanesulfonyloxy, trifluoromethanesulfonyloxy and ethanesulfonyloxy, arylsulfonyloxy groups such as benzenesulfonyloxy and p-toluenesulfonyloxy. Preferred "leaving groups" are halogens such as fluorine, chlorine, bromine and iodine.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Unless defined otherwise, all technical and scientific terms used herein have the standard meaning pertaining to the claimed subject matter belongs. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless otherwise indicated, conventional methods of mass spectroscopy, NMR, HPLC, protein chemistry, biochemistry, recombinant DNA techniques and pharmacology are employed. Unless specific definitions are provided, the standard nomenclature employed in connection with, and the standard laboratory procedures and techniques of, analytical chemistry, synthetic organic chemistry, and medicinal and pharmaceutical chemistry are employed. In certain instances, standard techniques are used for chemical syntheses, chemical analyses, pharmaceutical preparation, formulation, and delivery, and treatment of patients. In certain embodiments, standard techniques are used for recombinant DNA, oligonucleotide synthesis, and tissue culture and transformation (e.g., electroporation, lipofection). In some embodiments, reactions and purification techniques are performed e.g., using kits of manufacturer's specifications or as commonly accomplished or as described herein.

As used throughout this application and the appended claims, the following terms have the following meanings:

The term "alkyl" as used herein, means a straight, branched chain, or cyclic (in this case, it would also be known as "cycloalkyl") hydrocarbon containing from 1-10 carbon atoms. Illustrative examples of alkyl include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl.

The term "$C_1$-$C_6$-alkyl" as used herein, means a straight, branched chain, or cyclic (in this case, it would also be known as "cycloalkyl") hydrocarbon containing from 1-6 carbon atoms. Representative examples of alkyl include, but are not limited to, methyl, ethyl, n-propyl, iso-propyl, cyclopyl, n-butyl, sec-butyl, tert-butyl, cyclobutyl, n-pentyl, isopentyl, neopentyl, cyclopentyl, and n-hexyl.

The term "thioalkyl" as used herein, means an alkyl group, as defined herein, appended to the parent molecular moiety through a sulfur atom. Illustrative examples of thioalkyl include, but are not limited to, methylthio, ethylthio, butylthio, tert-butylthio, and hexylthio.

The term "halo" or "halogen" as used herein, means a —Cl, —Br, —I or —F.

As used herein, the term "sulfinyl" refers to a —S(=O)—R, where R is selected from the group consisting of alkyl, cycloalkyl, aryl, heteroaryl (bonded through a ring carbon) and heterocycloalkyl (bonded through a ring carbon).

As used herein, the term "sulfonyl" refers to a —S(=O)$_2$—R, where R is selected from the group consisting of alkyl, cycloalkyl, aryl, heteroaryl (bonded through a ring carbon) and heterocycloalkyl (bonded through a ring carbon).

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, and amino, including mono- and di-substituted amino groups, and the protected derivatives thereof. By way of example an optional substituents may be halide, —CN, —NO$_2$, or $L_sR_5$, wherein each $L_s$ is independently selected from a bond, —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$, —OC(=O)NH—, —NHC(=O)O—, or —($C_1$-$C_6$ alkylene)-; and each $R_5$ is selected from H, alkyl, fluoroalkyl, heteroalkyl, cycloalkyl, aryl, heteroaryl, or heterocycloalkyl. The protecting groups that may form the protective derivatives of the above substituents may be found in sources such as Greene and Wuts, above. In some embodiments, optional substituents are selected from halogen, —CN, —NH$_2$, —OH, —N(CH$_3$)$_2$, alkyl, fluoroalkyl, heteroalkyl, cycloalkyl, heterocycloalkyl, aryl, heteroaryl, alkoxy, aryloxy, alkylthio, arylthio, alkylsulfoxide, arylsulfoxide, alkylsulfone, and arylsulfone. In some embodiments, an optional substituents is halogen, —CN, —NH$_2$, —OH, —NH(CH$_3$), —N(CH$_3$)$_2$, alkyl, fluoroalkyl, heteroalkyl, alkoxy, fluoroalkoxy, —S-alkyl, or —S(=O)$_2$alkyl. In some embodiments, an optional substituent is selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, substituted groups are substituted with one of the preceding groups. In some embodiments, an optional substituent on an aliphatic carbon atom (acyclic or cyclic, saturated or unsaturated carbon atoms, excluding aromatic carbon atoms) includes oxo (=O).

The term "protected amine" refers to an amine with a removable protecting group which modifies the reactivity of an amine, against undesirable reaction during synthetic procedures and to be later removed. Examples of amine protecting groups include, but are not limited to, tert-butoxycarbonyl (Boc), 9-fluorenylmethyl carbonyl (Fmoc), triphenylmethyl (Tr) and carbobenzyloxy (Cbz). For example, to protect and activate the pyrimidine ring system with the 6-amino moiety in accordance with the present invention, bis-BOC, or bis-FMOC, CBZ, alloc, Teoc, methyl/ethyl-oxycarbonyl, bis-acetyl, or N-succinyl or N-phthaloyl may be used in addition to their mono-N protected analogs.

EXAMPLE

Example 1

Preparation of the Exemplary Cyclohexenone Compounds from *Antrodia Camphorata*

One hundred grams of mycelia, fruiting bodies or mixture of both from *Antrodia camphorata* were placed into a flask. A proper amount of water and alcohol (70-100% alcohol solution) was added into the flask and were stirred at 20-25° C. for at least 1 hour. The solution was filtered through a filter and 0.45 μm membrane and the filtrate was collected as the extract.

The filtrate of *Antrodia camphorata* was subjected to High Performance Liquid chromatography (HPLC) analysis. The separation was performed on a RP18 column, the mobile phase consisted of methanol (A) and 0.3% acetic acid (B), with the gradient conditions of 0-10 min in 95%-20% B, 10-20 min in 20%-10% B, 20-35 min in 10%-10% B, 35-40 min in 10%-95% B, at the flow rate of 1 ml/min. The column effluent was monitored with a UV-visible detector.

The fractions collected at 25 to 30 min were collected and concentrated to yield 4-hydroxy-2,3-dimethoxy-6-methyl-5-(3,7,11-trimethyldodeca-2,6,10-trienyl)cyclohex-2-enone (compound 1), a product of pale yellow brown liquid. The analysis of compound 1 showed the molecular formula of $C_{24}H_{38}O_4$, molecular weight of 390 with melting point of 48 to 52° C. NMR spectra showed that $^1$H-NMR (CDCl$_3$) δ (ppm)=1.51, 1.67, 1.71, 1.75, 1.94, 2.03, 2.07, 2.22, 2.25, 3.68, 4.05, 5.07, and 5.14; $^{13}$C-NMR (CDCl$_3$) δ (ppm)= 12.31, 16.1, 16.12, 17.67, 25.67, 26.44, 26.74, 27.00, 39.71, 39.81, 40.27, 43.34, 59.22, 60.59, 120.97, 123.84, 124.30, 131.32, 135.35, 135.92, 138.05, 160.45, and 197.12.

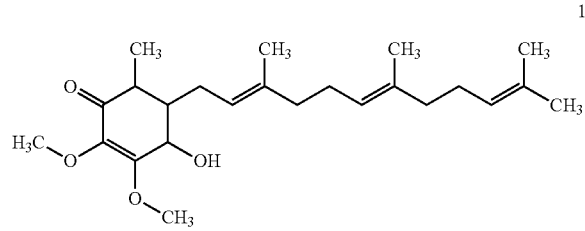 [SMILES: COC1=C(OC)C(O)C(C/C=C(\C)CC/C=C(\C)CCC=C(C)C)C(C)C1=O]

Compound 1: 4-hydroxy-2,3-dimethoxy-6-methyl-5-(3,7,11-trimethyldodeca-2,6,10-trienyl)cyclohex-2-enone Compound 27, a metabolite of compound 1, was obtained from urine samples of rats fed with Compound 1 in the animal study. Compound 27 was determined to be 4-hydroxy-2,3-dimethoxy-6-methyl-5-(3-methyl-2-hexenoic acid)cyclohex-2-enone with molecular weight of 312 ($C_{16}H_{24}O_6$). Compound 25 which was determined as 2,3-dimethoxy-5-methyl-6-((2E,6E)-3,7,11-trimethyldodeca-2,6,10-trienyl)cyclohexa-2,5-diene-1,4-dione (molecular weight of 386.52, $C_{24}H_{34}O_4$), was obtained from the purification process.

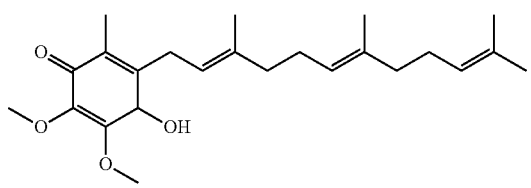

Compound 26, 4-hydroxy-2-methoxy-6-methyl-5-((2E,6E)-3,7,1-trimethyldodeca-2,6,10-trienyl)cyclohex-2-enone, was also prepared by purification process with molecular weight of 350.53 ($C_{23}H_{36}O_3$). Compound 28 was also prepared.

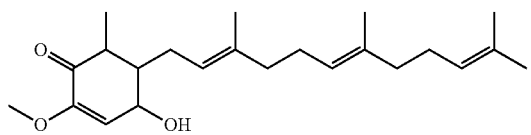

$^1$H (500 MHz; CD$_3$OD) δ 1.16 (3H, d, J=6.9 Hz), 1.58 (3H, s), 1.60 (3H, s), 1.62 (3H, s), 1.65 (3H, s), 1.77-1.83 (1H, m), 1.93-2.20 (2H, m), 2.00-2.20 (7H, m), 2.23-2.31 (1H, m), 2.63-2.71 (1H, m), 3.59 (3H, s), 4.64 (1H, dd, J=5.5 and 3.7 Hz), 5.07-5.12 (2H, m), 5.21 (1H, t, J=7.3 Hz), 5.91 (1H, d, J=5.7 Hz); $^{13}$C (125 MHz; CD$_3$OD) δ 13.1, 16.2, 17.8, 17.8, 25.9, 27.4, 27.8, 28.2, 40.9, 43.4, 47.5, 48.5, 49.8, 55.3, 65.0, 116.6, 123.3, 125.3, 125.4, 132.1, 136.0, 138.1, 152.0, 198.7.

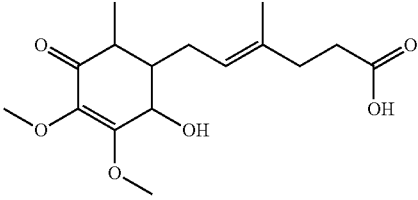

$[\alpha]^{24}_D$ 66.9 (c 0.69, MeOH); $^1$H (600 MHz; CD$_3$OD) δ 1.14 (3H, d, J=6.9 Hz), 1.65-1.70 (1H, m), 1.67 (3H, s), 2.24 (2H, t, J=7.4 Hz), 2.32 (2H, t, J=7.4 Hz), 2.43 (2H, t, J=7.4 Hz), 2.44-2.50 (m, 1H), 3.57 (3H, s), 4.04 (3H, s), 4.36 (1H, d, J=3.5 Hz), 5.29 (1H, t, J=7.1 Hz); $^{13}$C (150 MHz; CD$_3$OD) δ 12.8, 16.2, 28.1, 33.8, 35.8, 41.4, 45.6, 58.6, 60.7, 66.8, 123.4, 137.1, 137.2, 164.9, 177.3, 199.4.

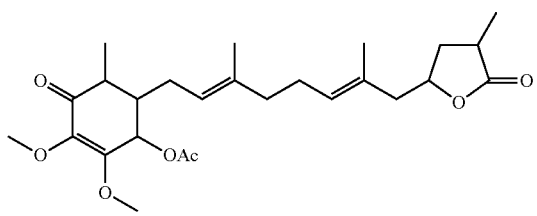

EI-MS, m/z 486 [M+Na]$^+$; $^1$H (600 MHz; CD$_3$OD) δ 1.19 (3H, d, J=7.0 Hz), 1.24 (3H, d, J=7.4 Hz), 1.60 (3H, s), 1.69 (3H, s), 1.93-2.00 (2H, m), 2.00-2.04 (1H, m), 2.05-2.08 (2H, m), 2.11 (3H, s), 2.13-2.20 (2H, m), 2.20-2.25 (m, 1H), 2.26-2.31 (2H, m), 2.40 (1H, dd, J=13.8 Hz and 7.0 Hz), 2.50-2.56 (1H, m), 2.73-2.80 (1H, m), 3.63 (3H, s), 4.00 (3H, s), 4.69-4.74 (1H, m), 5.17 (1H, t, J=6.7 Hz), 5.31 (1H, t, J=7.0 Hz), 5.75 (1H, d, J=3.1 Hz); $^{13}$C (150 MHz; CD$_3$OD) δ 13.1, 16.0, 16.2, 16.5, 20.9, 27.1, 28.0, 35.0, 35.6, 40.5, 42.5, 44.2, 45.9, 60.3, 61.1, 70.4, 78.8, 122.5, 129.2, 131.7, 138.3, 138.7, 160.5, 171.4, 182.7, 199.0.

Example 2

Preparation of Exemplary Cyclohexenone Core

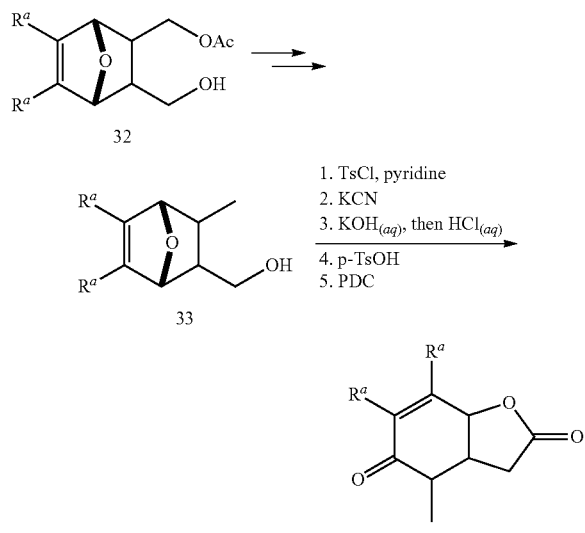

$R^a$ = H, CH$_3$, OMe, OBn

Compound 33 ($R^a$=H) was prepared by a known method (e.g., *J. Org. Chem.* 2004, 69, 8789-8795) from compound 32. The exemplary intermediate 34a ($R^a$=H) was prepared by the following steps. Other exemplary core intermediates (34b-d, $R^a$=CH$_3$, OMe, OBn, respectively, or the like) can be prepared accordingly.

Step 1. Preparation of (1R,2R,3R,4S)-3-methyl-7-oxabicyclo[2.2.1]hept-5-en-2-yl)methyl 4-methyl-benzene-1-sulfonate

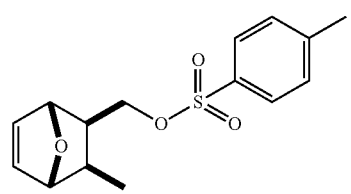

To a solution of Compound 21 (8.3 g, 59 mmol) in CH$_2$Cl$_2$ (210 mL) at ice bath were added Et$_3$N (21.0 mL, 148 mmol), 4-DMAP (1.0 g, 8.9 mmol), and TsCl (16.9 g, 88.8 mmol). The mixture was allowed to warm to room temperature and stirred for 16 h, washed with H$_2$O (100 mL×3) and brine (100 mL). The organic layer was dried over Na$_2$SO$_4$ and concentrated in vacuo. The residue was purified by column chromatography on silica gel (EtOAc:hexane, 1:3, R$_f$ 0.46) to provide 14.8 g (50.2 mmol, 85%) as a colorless oil. EI-MS, m/z 317 [M+Na]$^+$; [α]$^{24}_D$ −14.8 (c 2.34, CHCl$_3$); $^1$H (600 MHz; CDCl$_3$) δ 1.04 (3H, d, J=7.3 Hz), 1.83-1.90 (1H, m), 1.91-1.97 (1H, m), 2.51 (3H, s), 4.02 (1H, t, J=9.8 Hz), 4.22 (1H, dd, J=9.5 and 5.4 Hz), 4.49 (1H, s), 4.75 (1H, s), 6.32 (1H, dd, J=5.8 Hz and 1.6 Hz), 6.41 (1H, dd, J=5.8 and 1.6 Hz), 7.43 (2H, d, J=8.2 Hz), 7.87 (2H, d, J=8.2 Hz); $^{13}$C (150 MHz; CDCl$_3$) δ 14.1, 21.4, 33.6, 39.2, 71.0, 80.0, 84.5, 127.6, 129.7, 132.6, 134.4, 135.9, 144.7.

Step 2. Preparation of 2-[(1R,2S,3R,4S)-3-methyl-7-oxabicyclo[2.2.1]hept-5-en-2-yl]acetonitrile

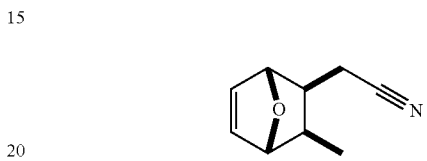

To a solution of Compound 21 (8.3 g, 59 mmol) in CH$_2$Cl$_2$ (210 mL) at ice bath were added Et$_3$N (21.0 mL, 148 mmol), 4-DMAP (1.0 g, 8.9 mmol), and TsCl (16.9 g, 88.8 mmol). The mixture was allowed to warm to room temperature and stirred for 16 h, washed with H$_2$O (100 mL×3) and brine (100 mL). The organic layer was dried over Na$_2$SO$_4$ and concentrated in vacuo. The residue was purified by column chromatography on silica gel (EtOAc:hexane, 1:3, R$_f$ 0.46) to provide 14.8 g (50.2 mmol, 85%) as a colorless oil. EI-MS, m/z 317 [M+Na]$^+$; [α]$^{24}_D$ −14.8 (c 2.34, CHCl$_3$); $^1$H (600 MHz; CDCl$_3$) δ 1.04 (3H, d, J=7.3 Hz), 1.83-1.90 (1H, m), 1.91-1.97 (1H, m), 2.51 (3H, s), 4.02 (1H, t, J=9.8 Hz), 4.22 (1H, dd, J=9.5 and 5.4 Hz), 4.49 (1H, s), 4.75 (1H, s), 6.32 (1H, dd, J=5.8 Hz and 1.6 Hz), 6.41 (1H, dd, J=5.8 and 1.6 Hz), 7.43 (2H, d, J=8.2 Hz), 7.87 (2H, d, J=8.2 Hz); $^{13}$C (150 MHz; CDCl$_3$) δ 14.1, 21.4, 33.6, 39.2, 71.0, 80.0, 84.5, 127.6, 129.7, 132.6, 134.4, 135.9, 144.7.

Step 3. Preparation of 2-[(1R,2S,3R,4S)-3-methyl-7-oxabicyclo[2.2.1]hept-5-en-2-yl]acetic acid

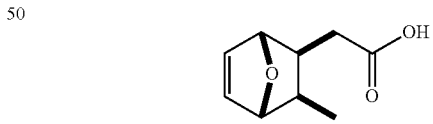

The nitrile (6.7 g, 45 mmol) prepared in Step 2 was heated to reflux for 4 h in 1N potassium hydroxide solution (480 mL, 480 mmol). After 4 h, the mixture was concentrated. The residue was allowed to cool to ice bath, acidified to pH 1 with conc. HCl$_{(aq)}$, and extracted with EtOAc (300 mL×3). The combined organic fractions were dried over Na$_2$SO$_4$ and concentrated in vacuo to yield acid (7.4 g, 44 mmol, 98%). TLC R$_f$ 0.63 (EtOAc:hexane, 2:1); EI-MS, m/z 191 [M+Na]$^+$; [α]$^{24}_D$ −7.03 (c 1.95, CHCl$_3$); $^1$H (600 MHz; CDCl$_3$) δ 1.00 (3H, d, J=7.3 Hz), 1.77-1.84 (1H, m), 1.98-2.04 (1H, m), 2.39 (1H, dd, J=16.9 and 10.0 Hz), 2.51 (1H, dd, J=16.9 and 5.4

Hz), 4.45 (1H, s), 4.65 (1H, s), 6.31 (2H, s); $^{13}$C (150 MHz; CDCl$_3$) δ 15.3, 33.5, 34.0, 35.9, 82.8, 84.8, 135.1, 135.6, 179.2.

Step 4. Preparation of (3aS,4R,7aR)-4-methyl-2,3, 3a,4,5,7a-hexahydro-1-benzofuran-2,5-dione

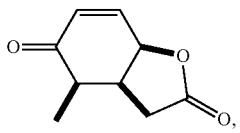

34a

A solution of acid (500 mg, 2.97 mmol) resulted from Step 3 and p-TSA (57 mg, 0.30 mmol) in toluene (20 mL) was heated at 100° C. for 3 h. After 3 h, the mixture was concentrated in vacuo to yield hydroxyl lactone compound 35a (450 mg); TLC R$_f$ 0.46 (EtOAc:hexane, 2:1); EI-MS, m/z 191[M+Na]$^+$.

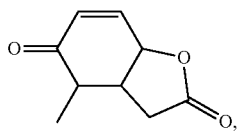

(35a)

To a stirred solution of crude hydroxyl lactone 35a (450 mg) in CH$_2$Cl$_2$ (15 mL) was added PDC (2.0 g, 5.4 mmol). The mixture was stirred at room temperature overnight, diluted with EtOAc (30 mL), and filtered. The residue was concentrated in vacuum and purified by column chromatography on silica gel (EtOAc:hexane, 1:1, TLC R$_f$ 0.38) to provide compound 34a, 294 mg (1.77 mmol, 60%, 2 steps) as white solids; EI-MS, m/z 189 [M+Na]$^+$; [α]$^{24}_D$ −269.3 (c 2.03, CHCl$_3$); $^1$H (600 MHz; CDCl$_3$) δ 1.15 (3H, d, J=6.9 Hz), 2.17 (1H, dd, J=17.4 and 12.7 Hz), 2.53 (1H, dd, J=17.4 and 8.5 Hz), 2.78 (1H, dd, J=6.7 and 5.5 Hz), 3.26-3.35 (1H, m), 5.32 (1H, dt, J=7.2 and 1.9 Hz), 6.18 (1H, dd, J=10.3 and 1.3 Hz), 6.68 (1H, dt, J=10.3 and 1.9 Hz); $^{13}$C (150 MHz; CDCl$_3$) δ 12.9, 29.6, 41.1, 75.2, 131.1, 141.1, 174.4, 197.7.

Example 3

Preparation of an Exemplary Compound 36a from Lactone 35a

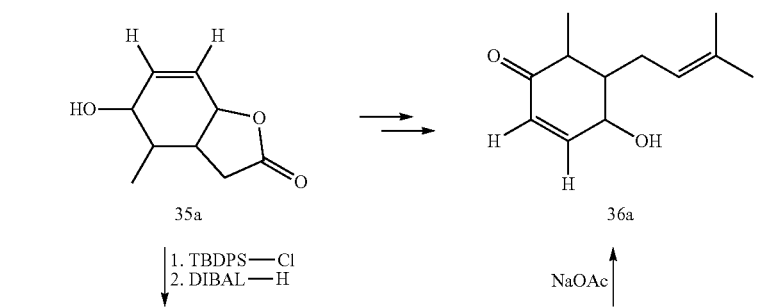

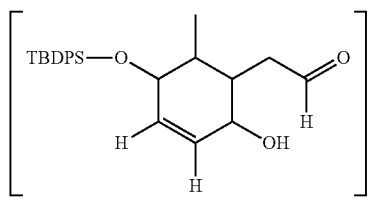

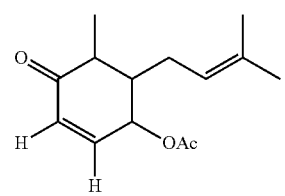

-continued

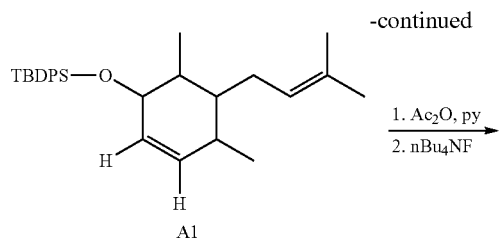 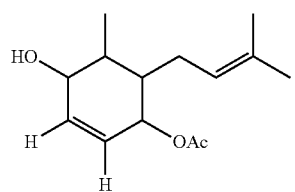

Compound 36a was prepared from Compound 35a under the following steps. The hydroxyl group was first protected with t-butyldiphenylsilyl chloride (TBDPS-Cl) (other non-limited exemplary suitable hydroxyl protecting groups that are inert to strong basic conditions can be used as well, e.g., MOM, MEM, THP protecting groups, or the like). The resulted compound was then first reduced by DIBAL-H and then reacted with Ph₃PCH(CH₃)(CH₃)I (Wittig reaction) under the basic condition (n-BuLi) to afford the intermediate A1. The hydroxyl group of the intermediate A1 was first protected with Acetate (condition: Ac₂O, pyridine) and then the silyl protecting group TBDPS was removed by n-Bu₄NF. The naked hydroxyl group was then oxidized with PDC to afford Compound B1. Deprotection of the acetate group afforded Compound 36a. A series of Compound 36 can be prepared similarly.

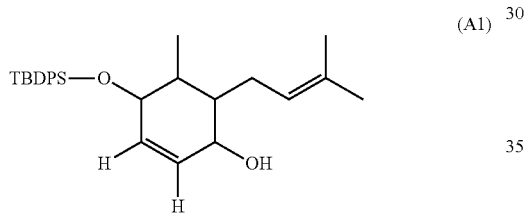

(A1)

$^1$H (600 MHz; (CD$_3$Cl) δ 0.77 (3H, d, J=7.3 Hz), 1.07 (9H, s), 1.65 (3H, s), 1.73 (3H, s), 1.84-1.90 (1H, m), 2.02-2.10 (1H, m), 2.21-2.28 (2H, m), 3.93 (1H, t, J=4.0 Hz), 4.18 (1H, br), 5.20-5.25 (1H, m), 5.66 (1H, dd, J=9.9 Hz and 4.5 Hz), 5.85 (1H, dd, J=9.9 Hz and 4.0 Hz), 7.37-7.41 (4H, m), 7.42-7.46 (2H, m), 7.66-7.70 (4H, m).

Example 4

Preparation of Exemplary Compound 37a and 37b from Compound 36

The desired Compounds 37a and 37b were prepared by reaction with R₂X (X is a leaving group such as halogen or tosylate) with concentrated HCl in aqueous solution.

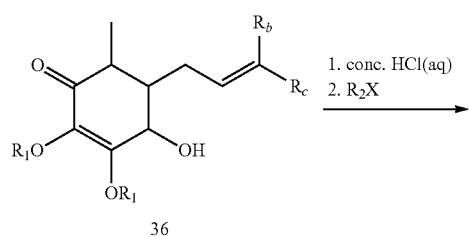

36

-continued

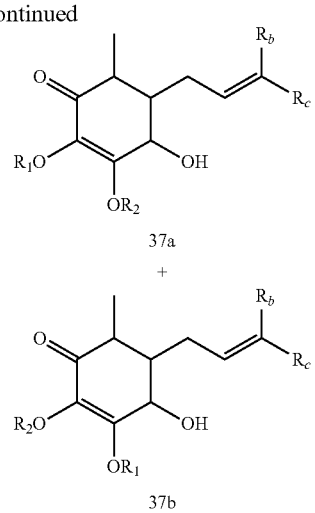

37a

+

37b

The following compounds were prepared accordingly.

Compound 31: 3-(benzyloxy)-4-hydroxy-2-methoxy-6-methyl-5-[(2E,6E)-3,7,11-trimethyldodeca-2,6,10-trien-1-yl]cyclohex-2-en-1-one

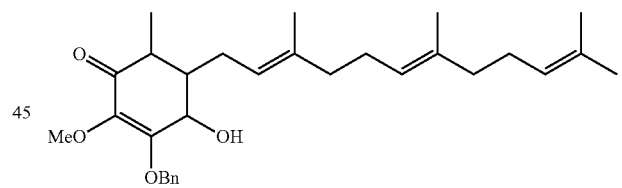

To (4S,5S,6S)-4-hydroxy-2,3-dimethoxy-6-methyl-5-[(2E,6E)-3,7,11-trimethyldo-deca-2,6,10-trien-1-yl]cyclohex-2-en-1-one (10.0 g, 25.6 mmol) in MeOH 50 mL was cooled to 0° C., conc. HCl$_{(aq)}$ (22.5 mL, 270 mmol) was added. The reaction was stirred at room temperature for 30 min. After 30 min, the mixture was concentrated in vacuo. The residue was diluted with EtOAc (100 mL), washed with sat. NaHCO₃ (50 mL×3) and brine (50 mL), dried over Na₂SO₄, filtered, concentrated and purified by column chromatography on silica gel (EtOAc:hexane, 1:5, TLC R$_f$ 0.26) to get product 3.0 g (6.4 mmol, 25%); EI-MS, m/z 489 [M+Na]$^+$; [α]$^{24}_D$ +18.6 (c 2.19, CHCl₃); $^1$H (500 MHz; CDCl₃) δ 1.16 (3H, d, J=7.0 Hz), 1.59 (6H, s), 1.64 (3H, s), 1.67 (3H, s), 1.73-1.75 (1H, m), 1.94-2.00 (2H, m), 2.00-2.09 (7H, m), 2.21-2.24 (2H, m), 2.52-2.56 (1H, m), 3.66 (3H, s), 4.35 (1H, t, J=3.6 Hz), 5.5-5.10 (2H, m), 5.12 (1H, t, J=7.0 Hz), 5.28 (1H, d, J=11.9 Hz), 5.44 (1H, d, J=11.9 Hz), 7.34-7.39 (5H, m); $^{13}$C (125 MHz; CDCl₃) δ 12.4, 16.0, 16.1, 17.7, 25.7, 26.5, 26.7, 26.9, 39.7, 39.8, 40.4, 43.4, 60.4, 68.1, 73.4, 121.0, 123.9, 124.3, 127.8, 128.4, 128.6, 131.2, 135.2, 136.3, 136.8, 137.9, 159.8, 197.3.

Compound 30: 2-(benzyloxy)-4-hydroxy-3-methoxy-6-methyl-5-[(2E,6E)-3,7,11-trimethyldodeca-2,6,10-trien-1-yl]cyclohex-2-en-1-one

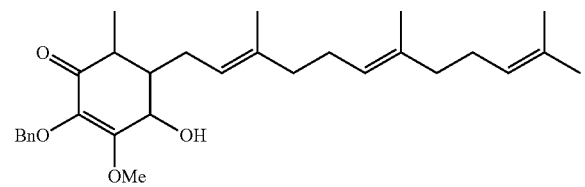 [SMILES: COC1=C(OCc2ccccc2)C(=O)C(C)C(C/C=C(\C)CC/C=C(\C)CCC=C(C)C)C1O]

6.1 g (13 mmol, 50%); TLC $R_f$ 0.26 (EtOAc:hexane, 1:5); EI-MS, m/z 489 [M+Na]$^+$; $[\alpha]^{24}_D$ −8.04 (c 2.04, CHCl$_3$); $^1$H (600 MHz; CDCl$_3$) δ 1.28 (3H, d, J=7.3 Hz), 1.49 (3H, s), 1.55 (3H, s), 1.57 (3H, s), 1.65 (s, 3H), 1.67-1.77 (m, 1H), 1.90-1.99 (2H, m), 1.94-1.99 (2H, m), 1.99-2.05 (4H, m), 2.05-2.10 (1H, m), 2.21-2.23 (1H, m), 2.61-2.65 (1H, m), 3.57 (1H, br), 3.67 (3H, s), 4.97-5.00 (1H, m), 5.03-5.06 (2H, m), 5.19 (1H, d, J=11.9 Hz), 5.46 (1H, d, J=11.9 Hz), 7.32-7.36 (5H, m); $^{13}$C (150 MHz; CDCl$_3$) 15.9, 16.0, 17.6, 17.7, 24.0, 25.6, 26.4, 26.7, 35.4, 39.6, 39.7, 44.9, 60.5, 70.8, 73.4, 121.8, 123.9, 124.3, 127.7, 128.4, 128.6, 131.2, 133.7, 135.1, 136.5, 137.9, 165.7, 195.1.

Compound 29: 2,3-dimethoxy-5-methyl-4-oxo-6-[(2E,6E)-3,7,11-trimethyldodeca-2,6,10-trien-1-yl]cyclohex-2-en-1-yl acetate

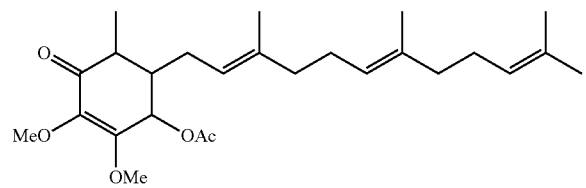 [SMILES: COC1=C(OC)C(OC(C)=O)C(C/C=C(\C)CC/C=C(\C)CCC=C(C)C)C(C)C1=O]

To (4S,5S,6S)-4-hydroxy-2,3-dimethoxy-6-methyl-5-[(2E,6E)-3,7,1-trimethyldo-deca-2,6,10-trien-1-yl]cyclohex-2-en-1-one (500 mg, 1.38 mmol) in pyridine 5 mL was cooled to 0° C., acetic anhydride (300 µL, 3.19 mmol) was added. The reaction was stirred at room temperature for 4 h. After 4 h, the mixture was diluted with EtOAc (20 mL), washed with 1N HCl$_{(aq)}$ (10 mL×2), sat. NaHCO$_3$ (10 mL×2), brine (20 mL), dried over Na$_2$SO$_4$, filtered, concentrated and purified by column chromatography on silica gel (EtOAc: hexane, 1:3, TLC $R_f$ 0.56) to get product 404 mg (0.934 mmol, 68%); EI-MS, m/z 433 [M+H]$^+$; $^1$H (500 MHz; CDCl$_3$) δ 1.19 (3H, d, J=7.0 Hz), 1.56 (3H, s), 1.59 (6H, s), 1.66 (3H, s), 1.83-1.90 (1H, m), 1.92-2.10 (10H, m), 2.08 (3H, s), 2.20-2.38 (1H, m), 2.48-2.56 (1H, m), 3.66 (3H, s), 3.98 (3H, s), 5.06-5.13 (3H, m), 5.74 (1H, d, J=3.2 Hz).

Example 5

Preparation of Exemplary Compound 1 Via Enolate Reaction

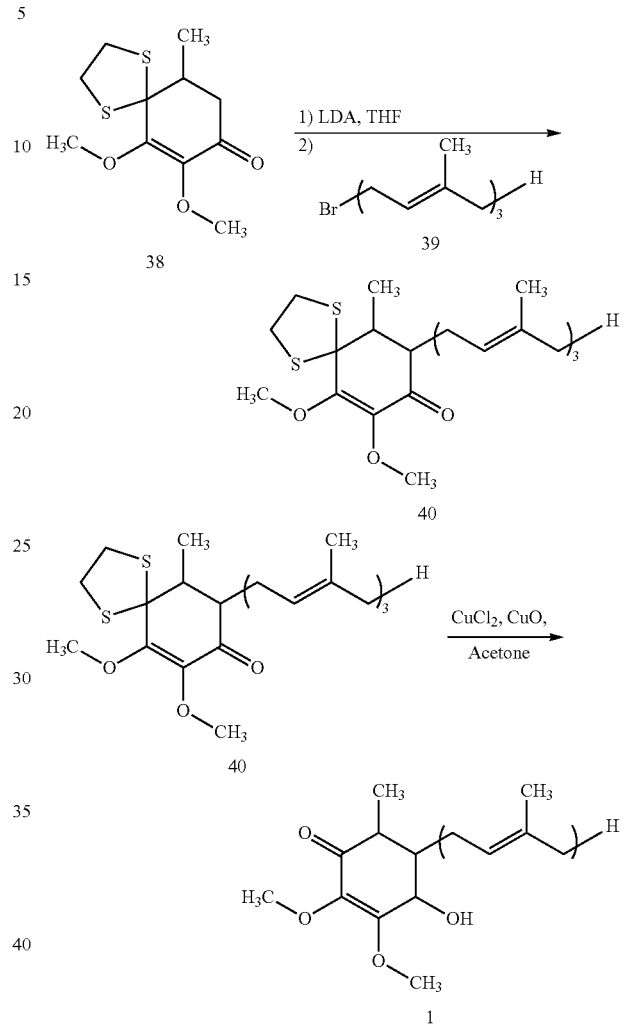

Compound 38 is prepared from 2,3-dimethoxy-5-methyl-cyclohex-2-ene-1,4-dione. In a reaction flask, compound 38 is slowly added to a solution of LDA in TI-IF at low temperature. After the formation of enolate, compound 39 is added slowly to the reaction mixture under inner gas condition. The reaction is quenched with water at low temperature and purified to afford compound 40. Deprotection of compound 40 with suitable reagents such as CuCl$_2$, CuO in acetone to afford compound 1.

Example 6

Determining the Cytotoxic Effects of Exemplary Cyclohexenone Compounds 25-31 Against Compound 1

Cell viability was measured using Cell Counting Kit-8 (CCK-8, Enzo Life Sciences, Farmingdale, N.Y.). In this assay, WST-8 is reduced by dehydrogenases in cells to produce a yellow-colored product (formazan), which is soluble in culture medium. The amount of formazan generated is directly proportional to the number of living cells. After treatment, CCK-8 solution was added to each well and incubated for 4 h. The concentration of formazan was measured with a spectrophotometer at an absorbance wavelength of 450 nm. Cell viability was expressed as a percentage of the corresponding control.

To determine whether the cytotoxic effects of Compound 1 correlate with the presence of Ras mutations, cell lines derived from human lung cancer (A549 and H838), liver cancer (HepG2 and Hep3B), and leukemia (K562 and THP-1) with wild-type Ras (H838, Hep3B, and K562) or mutant Ras (A549, HepG2, and THP-1) were used. Cell viability was measured after 48 h of Compound 1 treatment. The cell lines and their $IC_{50}$s in increasing order were THP-1 (2.22 µM)<A549 (3.24 µM)<H838 (3.32 µM)<Hep3B (3.74 µM)<K562 (5.12 µM)<HepG2 (6.42 µM) (See Table 1).

Next, the $IC_{50}$ values for Compound 1 analogs (Compounds 29, 30 and 31), a metabolite (Compound 27), and analogues isolated from filamentous *A. camphorata* (Compounds 25, 26, 28) were determined in H838 cells. The results indicated that the 2'-hydroxy group and the farnesyl group of Compound 1 were important for its cytotoxic effects. Further, Compound 31 was even more cytotoxic than Compound 1. (Table 1)

TABLE 1

$IC_{50}$ values of exemplary compounds of formula X determined by CCK-8 cell viability assay.

| Compound | A549 | H838 | Hep3B | HepG2 | K562 | THP-1 |
|---|---|---|---|---|---|---|
| 1 | 3.24 ± 0.35 | 2.96 ± 0.05 | 3.74 ± 0.35 | 6.42 ± 0.08 | 5.12 ± 0.83 | 2.22 ± 0.03 |
| 25 | — | 22.56 ± 6.45 | — | — | — | — |
| 26 | — | 11.34 ± 4.17 | — | — | — | — |
| 27 | — | >100 | — | — | — | — |
| 28 | — | >100 | — | — | — | — |
| 29 | — | >100 | — | — | — | — |
| 30 | 22.61 ± 2.24 | 25.56 ± 6.54 | 9.06 ± 3.03 | 27.03 ± 6.06 | — | — |
| 31 | 6.68 ± 0.75 | 3.41 ± 1.43 | 7.46 ± 7.06 | 8.98 ± 0.97 | — | — |

Values were presented as means ± S.E.M.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of formula X:

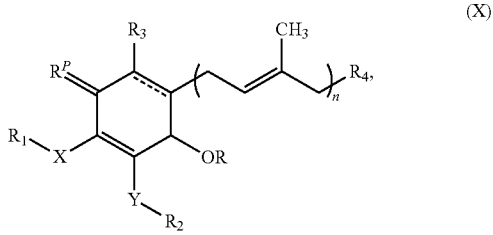

(X)

or a pharmaceutically acceptable salt, metabolite, solvate or prodrug thereof, wherein each of X and Y independently is a bond, oxygen, $NR_5$ or sulfur, with the proviso that X and Y are not a bond at the same time;

R is H, $C(=O)OR_5$, $C(=O)R_5$, $C(=O)NR_5R_6$, $C(=O)SR_5$, $C(=S)R_5$, or $C(=S)NR_5R_6$;

each of $R_1$, $R_2$ and $R_3$ independently is H, or an optionally substituted $C_1$-$C_{12}$alkyl, wherein when each of X and Y independently is oxygen, $NR_5$ or sulfur, $R_1$, and $R_2$ independently is an aryl or heteroaryl substituted $C_1$-$C_{12}$alkyl;

$R_4$ is H, $NR_5R_6$, $OR_5$, $OC(=O)R_7$, $C(=O)OR_5$, $C(=O)R_5$, $C(=O)NR_5R_6$, halogen, 5 or 6-membered lactone, $C_1$-$C_8$alkyl, $C_2$-$C_8$alkenyl, $C_2$-$C_8$alkynyl, aryl, glucosyl, wherein the 5 or 6-membered lactone, $C_1$-$C_8$alkyl, $C_2$-$C_8$alkenyl, $C_2$-$C_8$alkynyl, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently H or $C_1$-$C_8$alkyl;

$R_7$ is a $C_1$-$C_8$alkyl, $OR_5$ or $NR_5R_6$; the dotted line denotes an optionally present bond;

and n=1-12, provided when X and Y are oxygen, each of $R_1$ and $R_2$ independently is a substituted $C_1$-$C_{12}$alkyl.

2. The compound of claim 1, wherein R is a hydrogen, $C(=O)C_3H_7$, $C(=O)C_2H_5$, or $C(=O)CH_3$.

3. The compound of claim 1, wherein each of $R_1$, $R_2$ and $R_3$ independently is hydrogen, methyl, ethyl, propyl, butyl, pentyl, hexyl, heptyl, or octyl optionally substituted with a aryl or heteroaryl.

4. The compound of claim 3, wherein each of $R_1$, and $R_2$ is methyl substituted with phenyl.

5. The compound of claim 1, wherein $R_4$ is halogen, $NH_2$, $NHCH_3$, $N(CH_3)_2$, $OCH_3$, $OC_2H_5$, $C(=O)CH_3$, $C(=O)C_2H_5$, $C(=O)OCH_3$, $C(=O)OC_2H_5$, $C(=O)NHCH_3$, $C(=O)NHC_2H_5$, $C(=O)NH_2$, $OC(=O)CH_3$, $OC(=O)C_2H_5$, $OC(=O)OCH_3$, $OC(=O)OC_2H_5$, $OC(=O)NHCH_3$, $OC(=O)NHC_2H_5$, or $OC(=O)NH_2$.

6. The compound of claim 1, wherein $R_4$ is $C_2H_4C(CH_3)_2OH$, $C_2H_4C(CH_3)_2OCH_3$, $CH_2COOH$, $C_2H_4COOH$, $CH_2OH$, $C_2H_4OH$, $CH_2Ph$, $C_2H_4Ph$, $CH_2CH=C(CH_3)(CHO)$, $CH_2CH=C(CH_3)(C(=O)CH_3)$, 5 or 6-membered lactone, aryl, or glucosyl, wherein 5 or 6-membered lactone, aryl, and glucosyl are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

7. The compound of claim 1, wherein $R_4$ is $C_1$-$C_8$alkyl optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl.

8. The compound of claim 7, wherein $R_4$ is $CH_2CH\!=\!C(CH_3)_2$.

9. The compound of claim 1, wherein said compound is selected from group consisting of

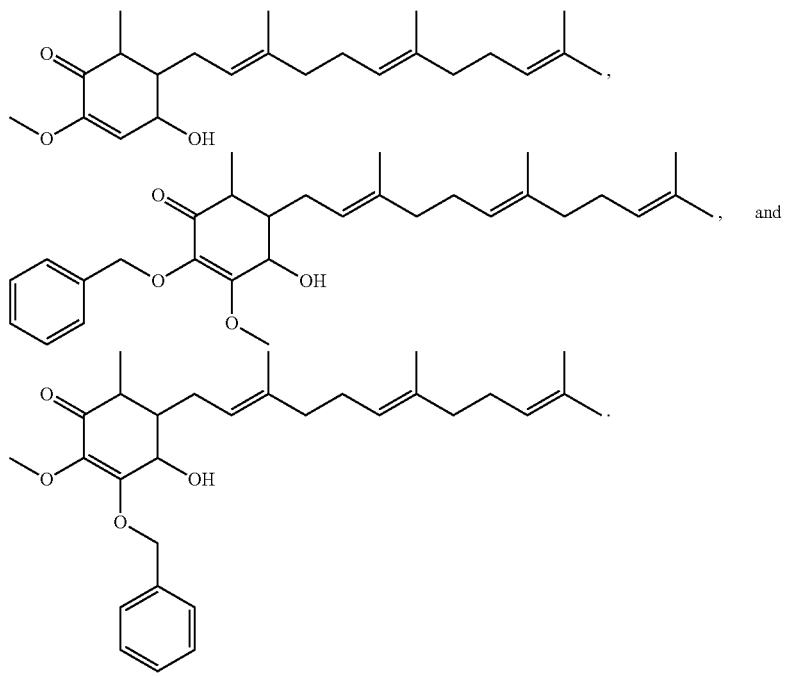

10. The compound of claim 2, wherein R is a hydrogen.

11. The compound of claim 3, wherein each of $R_1$, $R_2$ and $R_3$ independently is hydrogen, methyl, ethyl, propyl, butyl, pentyl, hexyl, heptyl, or octyl substituted with an aryl or heteroaryl.

12. The compound of claim 11, wherein $R_1$ is methyl substituted with phenyl.

13. The compound of claim 11, wherein $R_2$ is methyl substituted with phenyl.

* * * * *